US011197990B2

(12) United States Patent
Agarwal et al.

(10) Patent No.: US 11,197,990 B2
(45) Date of Patent: Dec. 14, 2021

(54) SYSTEMS AND METHODS FOR TRANSCUTANEOUS POWER TRANSFER USING MICRONEEDLES

(71) Applicant: TC1 LLC, St. Paul, MN (US)

(72) Inventors: Rahul Agarwal, San Jose, CA (US);
Gene Bornzin, Simi Valley, CA (US);
Edward Karst, Los Angeles, CA (US)

(73) Assignee: TC1 LLC, St. Paul, MN (US)

( * ) Notice: Subject to any disclaimer, the term of this patent is extended or adjusted under 35 U.S.C. 154(b) by 121 days.

(21) Appl. No.: 15/874,026

(22) Filed: Jan. 18, 2018

(65) Prior Publication Data

US 2018/0200423 A1    Jul. 19, 2018

Related U.S. Application Data

(60) Provisional application No. 62/471,494, filed on Mar. 15, 2017, provisional application No. 62/447,488, filed on Jan. 18, 2017.

(51) Int. Cl.
*A61N 1/05* (2006.01)
*A61M 60/80* (2021.01)
(Continued)

(52) U.S. Cl.
CPC ........ *A61M 60/871* (2021.01); *A61M 60/148* (2021.01); *A61N 1/048* (2013.01);
(Continued)

(58) Field of Classification Search
CPC ..... A61N 1/3787; A61M 1/086; A61M 1/372; A61M 1/127; A61M 1/122; H02J 50/12; H02J 5/005; H02J 50/80
See application file for complete search history.

(56) References Cited

U.S. PATENT DOCUMENTS 4,041,955 A    8/1977 Kelly et al.
4,352,960 A    10/1982 Dormer et al.
(Continued)

FOREIGN PATENT DOCUMENTS

DE    202012000166 U1    6/2013
DE    102012201073 A1    7/2013
(Continued)

OTHER PUBLICATIONS

Bonde et al.; Promise of unrestricted mobility with innovative, portable wireless powering of a mechanical circulatory assist device; American Association for Thoracic Surgery; ©2012; 2 pgs.; retrieved Mar. 12, 2014 from the internet: http://aats.org/annualmeeting/Abstracts/2012/T8.cgi.
(Continued)

*Primary Examiner* — Allen Porter
*Assistant Examiner* — Adreanne A. Arnold
(74) *Attorney, Agent, or Firm* — Armstrong Teasdale LLP

(57) ABSTRACT

A system for supplying power transcutaneously to an implantable device implanted within a subject is provided. The system includes an external connector including one of a microneedle array and a microwire holder. The system further includes a power cable electrically coupled to the external connector and configured to supply power to the one of the microneedle array and the microwire holder, and an internal connector configured to be implanted within the subject and electrically coupled to the implantable device, the internal connector including the other of the microneedle array and the microwire holder. The microneedle array includes a plurality of electrically conductive microneedles, the microwire holder includes a plurality of electrical contacts, and the microwire holder is configured to engage the microneedle array such that the plurality of electrically conductive microneedles extend through the skin of the (Continued)

subject and electrically couple to the plurality of electrical contacts.

14 Claims, 9 Drawing Sheets

(51) Int. Cl.
| | |
|---|---|
| *A61M 60/871* | (2021.01) |
| *H02J 7/02* | (2016.01) |
| *A61N 1/04* | (2006.01) |
| *A61N 1/378* | (2006.01) |
| *A61M 60/148* | (2021.01) |
| *H01R 13/52* | (2006.01) |
| *H02J 7/00* | (2006.01) |

(52) U.S. Cl.
CPC ......... *A61N 1/0476* (2013.01); *A61N 1/0502* (2013.01); *A61N 1/0504* (2013.01); *A61N 1/3787* (2013.01); *H02J 7/02* (2013.01); *A61M 2205/025* (2013.01); *A61M 2205/0205* (2013.01); *A61M 2205/0238* (2013.01); *A61M 2205/18* (2013.01); *A61M 2205/3523* (2013.01); *A61M 2205/3538* (2013.01); *A61M 2205/581* (2013.01); *A61M 2205/582* (2013.01); *A61M 2205/8206* (2013.01); *H01R 13/5224* (2013.01); *H02J 7/00* (2013.01)

(56) References Cited

U.S. PATENT DOCUMENTS

| | | | |
|---|---|---|---|
| 4,561,443 A | 12/1985 | Hogrefe et al. | |
| 4,561,444 A | 12/1985 | Livingston et al. | |
| 4,630,615 A | 12/1986 | Yomtov | |
| 4,679,560 A | 7/1987 | Galbraith | |
| 4,726,378 A | 2/1988 | Kaplan | |
| 4,736,747 A | 4/1988 | Drake | |
| 4,924,171 A | 5/1990 | Baba et al. | |
| 4,945,305 A | 7/1990 | Blood | |
| 5,070,223 A | 12/1991 | Colasante | |
| 5,205,286 A | 4/1993 | Soukup et al. | |
| 5,346,458 A | 9/1994 | Affeld | |
| 5,350,413 A | 9/1994 | Miller et al. | |
| 5,569,156 A | 10/1996 | Mussivand | |
| 5,630,836 A | 5/1997 | Prem et al. | |
| 5,690,693 A | 11/1997 | Wang et al. | |
| 5,695,471 A | 12/1997 | Wampler | |
| 5,702,431 A | 12/1997 | Wang et al. | |
| 5,708,346 A | 1/1998 | Schoeb | |
| 5,755,748 A | 5/1998 | Borza | |
| 5,771,438 A | 6/1998 | Palermo et al. | |
| 5,831,248 A | 11/1998 | Hojyo et al. | |
| 5,888,242 A | 3/1999 | Antaki et al. | |
| 5,948,006 A | 9/1999 | Mann | |
| 6,070,103 A * | 5/2000 | Ogden | A61N 1/372 607/60 |
| 6,071,093 A | 6/2000 | Hart | |
| 6,100,618 A | 8/2000 | Schoeb et al. | |
| 6,116,862 A | 9/2000 | Rau et al. | |
| 6,123,726 A | 9/2000 | Mori et al. | |
| 6,149,683 A | 11/2000 | Lancisi et al. | |
| 6,186,665 B1 | 2/2001 | Maher et al. | |
| 6,212,430 B1 | 4/2001 | Kung | |
| 6,234,772 B1 | 5/2001 | Wampler et al. | |
| 6,264,635 B1 | 7/2001 | Wampler et al. | |
| 6,296,533 B1 | 10/2001 | Grubbs et al. | |
| 6,312,338 B1 | 11/2001 | Sato et al. | |
| 6,320,354 B1 | 11/2001 | Sengupta et al. | |
| 6,324,431 B1 | 11/2001 | Zarinetchi et al. | |
| 6,327,504 B1 | 12/2001 | Dolgin et al. | |
| 6,334,856 B1 * | 1/2002 | Allen | A61B 5/14514 604/191 |
| 6,365,996 B2 | 4/2002 | Schob | |
| 6,389,318 B1 | 5/2002 | Zarinetchi et al. | |
| 6,400,991 B1 | 6/2002 | Kung | |
| 6,442,434 B1 | 8/2002 | Zarinetchi et al. | |
| 6,451,055 B1 | 9/2002 | Weiss | |
| 6,458,164 B1 | 10/2002 | Weiss | |
| 6,478,820 B1 | 11/2002 | Weiss | |
| 6,553,263 B1 | 4/2003 | Meadows et al. | |
| 6,579,315 B1 | 6/2003 | Weiss | |
| 6,591,139 B2 | 7/2003 | Loftin et al. | |
| 6,605,032 B2 | 8/2003 | Benkowski et al. | |
| 6,647,298 B2 | 11/2003 | Abrahamson et al. | |
| 6,650,213 B1 | 11/2003 | Sakurai et al. | |
| 6,688,861 B2 | 2/2004 | Wampler | |
| 6,723,039 B2 | 4/2004 | French et al. | |
| 6,772,011 B2 | 8/2004 | Dolgin | |
| 6,801,807 B2 | 10/2004 | Abrahamson | |
| 6,810,289 B1 | 10/2004 | Shaquer | |
| 6,850,803 B1 | 2/2005 | Jimenez et al. | |
| 6,894,456 B2 | 5/2005 | Tsukamoto et al. | |
| 6,895,281 B1 | 5/2005 | Amundson et al. | |
| 6,949,065 B2 | 9/2005 | Sporer et al. | |
| 6,960,968 B2 | 11/2005 | Odenaal et al. | |
| 6,967,621 B1 | 11/2005 | Cadotte, Jr. et al. | |
| 6,985,773 B2 | 1/2006 | Von Arx et al. | |
| 6,991,595 B2 | 1/2006 | Burke et al. | |
| 7,015,769 B2 | 3/2006 | Schulman et al. | |
| 7,107,103 B2 | 9/2006 | Schulman et al. | |
| 7,126,310 B1 | 10/2006 | Barron | |
| 7,225,032 B2 | 5/2007 | Schmeling et al. | |
| 7,246,040 B2 | 7/2007 | Borg et al. | |
| 7,286,880 B2 | 10/2007 | Olson et al. | |
| 7,428,438 B2 | 9/2008 | Parramon et al. | |
| 7,471,986 B2 | 12/2008 | Hatlestad | |
| 7,496,733 B2 | 2/2009 | Altman et al. | |
| 7,505,816 B2 | 3/2009 | Schmeling et al. | |
| 7,515,012 B2 | 4/2009 | Schulman et al. | |
| 7,522,878 B2 | 4/2009 | Baarman | |
| 7,532,901 B1 | 5/2009 | Lafranchise et al. | |
| 7,565,187 B1 | 7/2009 | Dynok et al. | |
| 7,571,007 B2 | 8/2009 | Erickson et al. | |
| 7,574,173 B2 | 8/2009 | Terranova et al. | |
| 7,587,241 B2 | 9/2009 | Parramon et al. | |
| 7,599,743 B2 | 10/2009 | Hassler, Jr. et al. | |
| 7,650,187 B2 | 1/2010 | Gruber et al. | |
| 7,650,192 B2 | 1/2010 | Wahlstrand | |
| 7,699,586 B2 | 4/2010 | Larose et al. | |
| 7,711,433 B2 | 5/2010 | Davis et al. | |
| 7,720,546 B2 | 5/2010 | Ginggen et al. | |
| 7,741,734 B2 | 6/2010 | Joannopoulos et al. | |
| 7,761,164 B2 | 7/2010 | Verhoef et al. | |
| 7,774,069 B2 | 8/2010 | Olson et al. | |
| 7,782,190 B1 | 8/2010 | Martin et al. | |
| 7,805,200 B2 | 9/2010 | Kast et al. | |
| 7,812,481 B2 | 10/2010 | Iisaka et al. | |
| 7,818,036 B2 | 10/2010 | Lair et al. | |
| 7,818,037 B2 | 10/2010 | Lair et al. | |
| 7,825,543 B2 | 11/2010 | Karalis et al. | |
| 7,830,114 B2 | 11/2010 | Reed | |
| 7,865,245 B2 | 1/2011 | Torgerson et al. | |
| 7,872,367 B2 | 1/2011 | Recksiek et al. | |
| 7,904,170 B2 | 3/2011 | Harding | |
| 7,932,696 B2 | 4/2011 | Peterson et al. | |
| 7,962,222 B2 | 6/2011 | He et al. | |
| 7,976,271 B2 | 7/2011 | Larose et al. | |
| 7,997,854 B2 | 8/2011 | Larose et al. | |
| 8,007,254 B2 | 8/2011 | Larose et al. | |
| RE42,682 E | 9/2011 | Barreras et al. | |
| 8,062,783 B2 | 11/2011 | Carter et al. | |
| 8,076,807 B2 | 12/2011 | Roland et al. | |
| 8,081,925 B2 | 12/2011 | Parramon et al. | |
| 8,096,954 B2 | 1/2012 | Stahmann et al. | |
| 8,140,168 B2 | 3/2012 | Olson et al. | |
| 8,150,529 B2 | 4/2012 | Snell et al. | |
| 8,152,493 B2 | 4/2012 | Larose et al. | |
| 8,165,694 B2 | 4/2012 | Carbanaru et al. | |
| 8,185,212 B2 | 5/2012 | Carbunaru et al. | |
| 8,193,766 B2 | 6/2012 | Rondoni et al. | |
| 8,203,434 B2 | 6/2012 | Yoshida | |
| 8,244,367 B2 | 8/2012 | Wahlstrand et al. | |

(56) References Cited

U.S. PATENT DOCUMENTS

| | | |
|---|---|---|
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,323,174 B2 | 12/2012 | Jeevanandam et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,449,444 B2 | 5/2013 | Poirier |
| 8,463,395 B2 | 6/2013 | Forsell |
| 8,489,200 B2 | 7/2013 | Zarinetchi et al. |
| 8,506,471 B2 | 8/2013 | Bourque |
| 8,545,436 B2 | 10/2013 | Robertson et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,588,884 B2 | 11/2013 | Hegde et al. |
| 8,597,350 B2 | 12/2013 | Rudser et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,652,024 B1 | 2/2014 | Yanai et al. |
| 8,657,733 B2 | 2/2014 | Ayre et al. |
| 8,668,473 B2 | 3/2014 | Larose et al. |
| 8,682,431 B2 | 3/2014 | Callaway et al. |
| 8,694,117 B2 | 4/2014 | Aghassian et al. |
| 8,794,989 B2 | 8/2014 | Kearsley et al. |
| 8,810,071 B2 | 8/2014 | Sauerlaender et al. |
| 8,858,416 B2 | 10/2014 | Crosby et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,091,271 B2 | 7/2015 | Bourque |
| 9,106,083 B2 | 8/2015 | Partovi |
| 9,114,238 B2 | 8/2015 | Singh et al. |
| 9,149,331 B2 | 10/2015 | Deem et al. |
| 9,166,347 B2 | 10/2015 | Sabin et al. |
| 9,192,704 B2 | 11/2015 | Yomtov et al. |
| 9,302,093 B2 | 4/2016 | Mashiach |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 10,388,142 B2 * | 8/2019 | Kimball ............... A61M 1/122 |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2002/0138049 A1 * | 9/2002 | Allen ............... A61B 5/150022 |
| | | 604/272 |
| 2003/0171792 A1 | 9/2003 | Zarinetchi et al. |
| 2004/0138725 A1 | 7/2004 | Forsell |
| 2004/0256146 A1 | 12/2004 | Frericks et al. |
| 2005/0006083 A1 | 1/2005 | Chen et al. |
| 2005/0071001 A1 | 3/2005 | Jarvik |
| 2005/0090883 A1 | 4/2005 | Westlund et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0078293 A1 | 4/2007 | Shambaugh, Jr. et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0021394 A1 | 1/2008 | Larose et al. |
| 2008/0027293 A1 | 1/2008 | Vodermayer et al. |
| 2008/0054638 A1 | 3/2008 | Greene et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0203957 A1 | 8/2009 | Larose et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0262135 A1 | 10/2010 | Berube |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec et al. |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234011 A1 | 9/2011 | Yi et al. |
| 2011/0234155 A1 | 9/2011 | Chen et al. |
| 2011/0241436 A1 | 10/2011 | Furukawa |
| 2011/0241750 A1 | 10/2011 | Hill |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0046514 A1 | 2/2012 | Bourque |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0095281 A1 | 4/2012 | Reichenbach et al. |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |

(56) References Cited

U.S. PATENT DOCUMENTS

| | | |
|---|---|---|
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0096364 A1 | 4/2013 | Reichenbach et al. |
| 2013/0096602 A1* | 4/2013 | Kumar ............... H01R 13/5219 606/191 |
| 2013/0119773 A1 | 5/2013 | Davis |
| 2013/0121821 A1 | 5/2013 | Ozaki et al. |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0170970 A1 | 7/2013 | Ozaki et al. |
| 2013/0190551 A1 | 7/2013 | Callaway et al. |
| 2013/0197607 A2 | 8/2013 | Wilder et al. |
| 2013/0204316 A1* | 8/2013 | Carpentier ........... A61B 8/0816 607/45 |
| 2013/0214731 A1 | 8/2013 | Dinsmoor et al. |
| 2013/0225909 A1 | 8/2013 | Dormanen et al. |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0303020 A1 | 11/2013 | Sabin et al. |
| 2013/0310630 A1 | 11/2013 | Smith et al. |
| 2013/0314047 A1 | 11/2013 | Eagle et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0073839 A1 | 3/2014 | Yomtov et al. |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2014/0324113 A1* | 10/2014 | Savage ............... A61N 1/3918 607/8 |
| 2015/0123654 A1 | 5/2015 | Gagnon et al. |
| 2015/0141910 A1* | 5/2015 | Francis ............. A61M 37/0015 604/46 |
| 2015/0207330 A1 | 7/2015 | Petersen |
| 2015/0207331 A1 | 7/2015 | Petersen |
| 2015/0222127 A1 | 8/2015 | Hansen et al. |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2015/0290374 A1 | 10/2015 | Bourque et al. |
| 2015/0290378 A1 | 10/2015 | Schade et al. |
| 2016/0064117 A1 | 3/2016 | Romero et al. |
| 2016/0135684 A1 | 5/2016 | Kappel et al. |
| 2016/0218432 A1 | 7/2016 | Pope et al. |
| 2016/0250484 A1 | 9/2016 | Nguyen et al. |
| 2016/0254703 A1 | 9/2016 | Hansen |
| 2016/0254704 A1 | 9/2016 | Hansen et al. |
| 2017/0246440 A1* | 8/2017 | Kalghatgi ................ A61L 2/14 |
| 2018/0256801 A1* | 9/2018 | Conyers ................ A61M 1/127 |

FOREIGN PATENT DOCUMENTS

| | | |
|---|---|---|
| EP | 0589608 A2 | 3/1994 |
| EP | 1513241 A1 | 3/2005 |
| EP | 2267864 A2 | 12/2010 |
| EP | 2878060 A1 | 6/2015 |
| GB | 2477034 A | 7/2011 |
| JP | H03109063 A | 5/1991 |
| JP | 11506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120077448 | 7/2012 |
| KR | 1020120007296 | 10/2012 |
| WO | 0001442 A2 | 1/2000 |
| WO | 0074747 A1 | 12/2000 |
| WO | 0137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014018965 A1 | 1/2014 |
| WO | 2014039673 A1 | 3/2014 |

OTHER PUBLICATIONS

Chargepoint, Inc.; -chargepoin+®; product brochure; 4 pgs.; ©2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600): Watertown, MA; 12 pgs.; 1988 (year of pub. sufficiently earlier than effective US filing date and any foreign priority date).

Evatran; Pluglessᵀᴹ Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the international Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

(56) References Cited

OTHER PUBLICATIONS

Merli, Francesco, et al.," The Effect of Insulating Layers on the Performance of Implanted Antennas", IEEE Transaction on Antennas and Propagation, vol. 59, No. 1, Jan. 2011, pp. 21-31.
Abadia, Javier, et al., 3D-Spiral Small Antenna Design and Realization for Biomdical Telemetry in the MICS Band. Radioengineering, vol. 18, No. 4, Dec. 2009, pp. 359-367.
Panasonic Lithium Ion UF553450Z Spec Sheet, 1 page.
Moazami, et al. Pump Replacement for Left Ventricular Assist Device Failure Can be Done Safely and Is Associated with Low Mortality. Ann Thorac Surg 2013;95;500-505.
Kalavrouziotis D., et al."Incidence and characterization of percutaneous lead damage in the Heartmate II left ventricular assist device" J Heart and Lung Transplantation 2013:32(4);S85.
http://www.mdpi.com/pharmaceutics/pharmaceutics-06-00220/article_deploy/html/images/pharmaceutics-06-00220-g001-1024.png.
International Search Report and Written Opinion for International Patent Application No. PCT/US2018/014150, dated Aug. 8, 2018, 16 pages.

\* cited by examiner

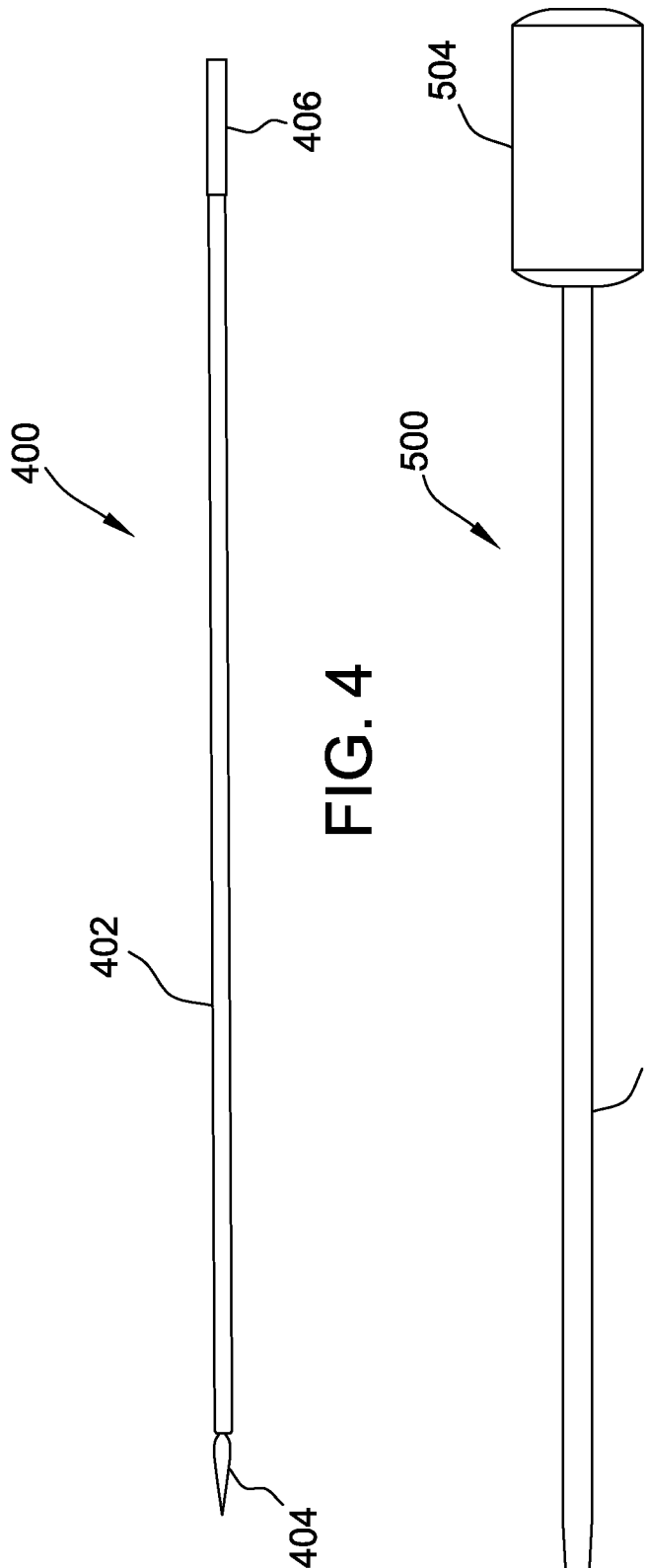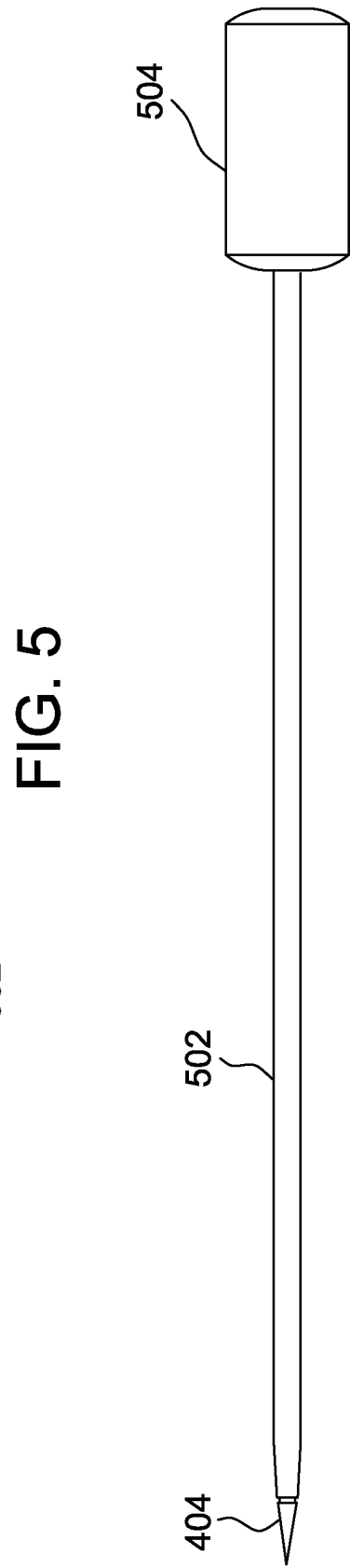
FIG. 4
FIG. 5
FIG. 6

SYSTEMS AND METHODS FOR TRANSCUTANEOUS POWER TRANSFER USING MICRONEEDLES

CROSS REFERENCE TO RELATED APPLICATIONS

This application claims priority to provisional application Ser. No. 62/447,488, filed Jan. 18, 2017, and provisional application Ser. No. 62/471,494, filed Mar. 15, 2017, both of which are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference for all purposes.

FIELD

This disclosure relates generally to methods and systems for transferring power transcutaneously, and in certain respects, using a plurality of conductors to transfer power.

BACKGROUND

Implantable medical devices such as pacemakers, ventricular assist devices (VADs), spinal cord stimulation (SCS) devices, and deep brain stimulation (DBS) devices require electric power to operate. That power may be provided, for example, by an internal battery (e.g., for pacemakers, SCS devices, and DBS devices), AC mains, or an external battery (e.g., for VADs).

Implanted batteries generally limit the amount of power that can be delivered to the implanted device. Further, implanted batteries may require surgical replacements. More recently, there has been a focus on developing systems for wirelessly transferring power to implanted batteries. Such systems, however, may be relatively inefficient, and have yet to be realized for high-powered devices such as VADs.

External batteries typically require a wired electrical connection to the implanted device that passes through the skin of the patient. In the example of VADs, percutaneous cables used to transfer power, data, or both through the skin are referred to as percutaneous drivelines. For such drivelines, it is desirable to provide a safe, relatively small connection through the skin. Further, it is desirable to prevent displacement of such drivelines.

Accordingly, it would be desirable to provide a transcutaneous power transfer system that provides transfer of power and/or data from the outside of the body to the inside of the body. There is a desire to improve existing mechanisms for transfer of power and/or data through the skin of a patient.

SUMMARY OF THE DISCLOSURE

In one embodiment, a system for supplying power transcutaneously to an implantable device implanted within a subject is provided. The system includes an external connector including one of a microneedle array and a microwire holder. The system further includes a power cable electrically coupled to the external connector and configured to supply power to the one of the microneedle array and the microwire holder from an external power source, and an internal connector configured to be implanted within the subject and electrically coupled to the implantable device, the internal connector including the other of the microneedle array and the microwire holder. The microneedle array includes a plurality of electrically conductive microneedles, the microwire holder includes a plurality of electrical contacts, and the microwire holder is configured to engage the microneedle array such that the plurality of electrically conductive microneedles extend through the skin of the subject and electrically couple to the plurality of electrical contacts. In various embodiments, the conductive microneedles are relatively thin structures having a conductive wire or element. In various embodiments, the microneedles are formed of a needle-like structure loaded with a conductive wire. The needle-like structure may an insulative body.

In one embodiment, a system for supplying power transcutaneously to an implantable device implanted within a subject is provided. The system includes a first microconductor configured to extend through the subject's skin, a second microconductor configured to extend through the subject's skin, wherein the first microconductor and the second microconductor are configured to receive and conduct power generated by an external power source, and a control unit configured to be implanted within the subject. The control unit includes a housing, a first electrical contact configured to electrically couple to the first microconductor, a second electrical contact configured to electrically couple to the second microconductor, control circuitry positioned within the housing and electrically coupled to the first and second electrical contacts, the control circuitry configured to control operation of the implantable device, and a driveline connector electrically coupled to the control circuitry, the driveline connector configured to transfer power and control signals to the implantable device through a driveline extending between the driveline connector and the implantable device.

In one embodiment, a method of implanting a transcutaneous power transfer system in a subject is provided, the transcutaneous power transfer system operable to supply power transcutaneously to an implantable device in the subject. The method includes implanting an internal connector within the subject, the internal connector including a microwire holder that includes a plurality of electrical contacts, connecting an external connector to the internal connector by inserting a plurality of electrically conductive microneedles through the skin of the subject such that the plurality of electrically conductive microneedles electrically couple to the plurality of electrical contacts, connecting a power cable to the external connector, and supplying power to the plurality of electrically conductive microneedles from an external power source using the power cable.

In one embodiment, a method of implanting a transcutaneous power transfer system in a subject is provided, the transcutaneous power transfer system operable to supply power transcutaneously to an implantable device in the subject. The method includes implanting a control unit within the subject, the control unit including a housing, a first electrical contact, a second electrical contact, and control circuitry configured to control operation of the implantable device, inserting a first microconductor through the skin of the subject such that the first microconductor electrically contacts the first electrical contact, inserting a second microconductor through the skin of the subject such that the second microconductor electrically contacts the second electrical contact, and supplying power to the first and second microconductors from an external power source.

In one embodiment, a method of forming a connection between an external connector and an internal connector in a transcutaneous power transfer system is provided. The method includes piercing skin of a subject with plurality of electrically conductive microneedles formed on the external connector, and placing the plurality of electrically conductive microneedles in contact with a plurality of electrical contacts formed on the internal connector.

In one embodiment, a system incorporating any of the above features is provided.

In one embodiment, a device incorporating any of the above features is provided.

Features that are described and/or illustrated with respect to one embodiment may be used in the same way or in a similar way in one or more other embodiments and/or in combination with or instead of the features of the other embodiments. That is, any feature described herein may be used in any of the embodiments described herein.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIG. 4 is a schematic diagram of a microconductor that may be used with the transcutaneous power transfer system shown in FIG. 3.

FIG. 5 is a schematic diagram of an injection tool that may be used to implant the microconductor shown in FIG. 4.

FIG. 6 is a schematic diagram of the microconductor shown in FIG. 4 loaded into the injection tool shown in FIG. 5.

DETAILED DESCRIPTION

Figure 1:
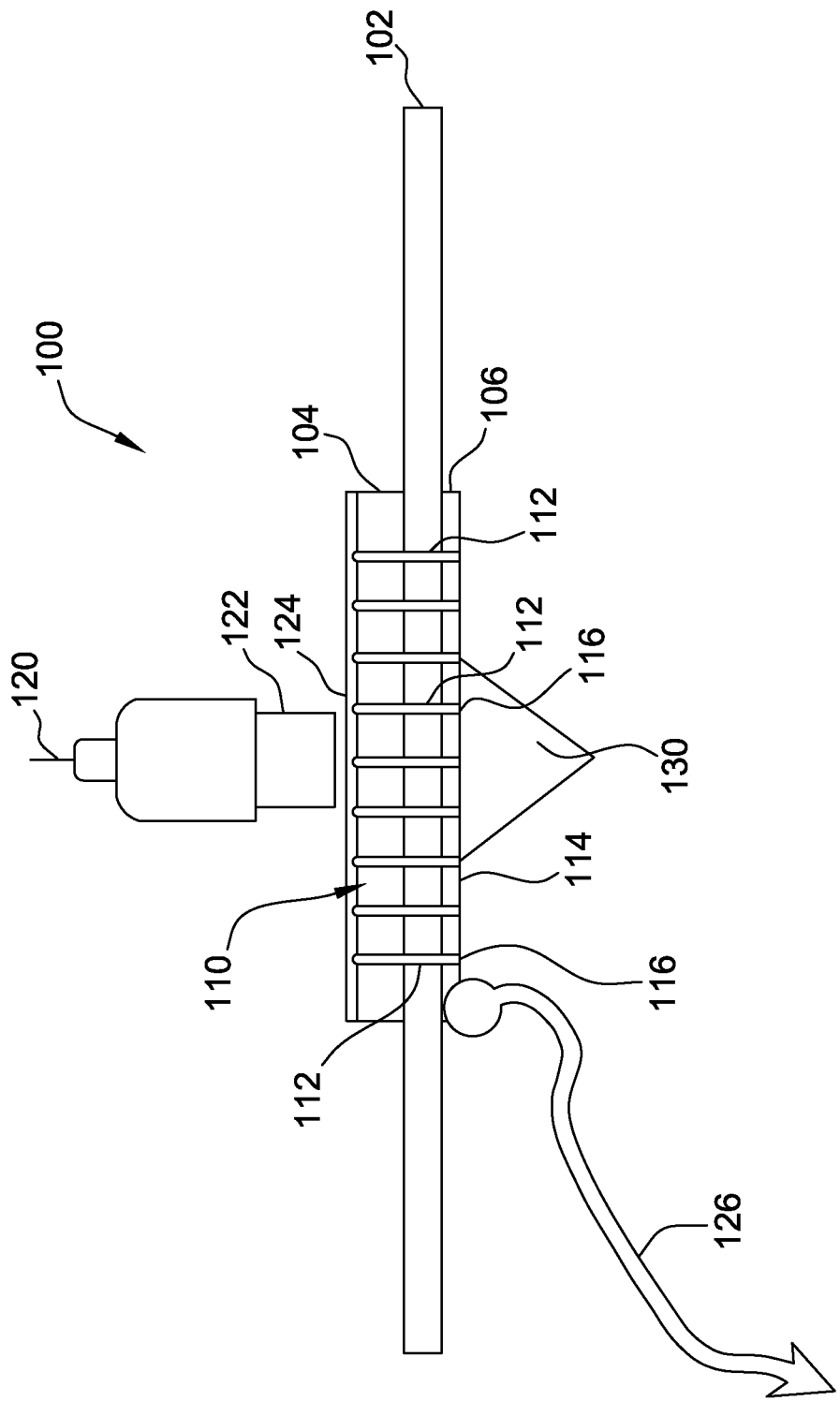
FIG. 1 is a schematic diagram of one embodiment of a transcutaneous power transfer system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

The systems and methods in certain embodiments include a transcutaneous power transfer system. The transcutaneous power transfer system includes electrical connections that pass through the subject's skin, but that are relatively small. In some embodiments, an electrical connection is formed using a plurality of parallel sub-passages that, when taken together, provide enough power to drive an implanted medical device or recharge an implanted battery. Each sub-passage is on a micro-scale such that it passes through pores already present in the skin, reducing irritation and risk of infection to the subject.

Turning now to FIG. 1, a transcutaneous power transfer system is indicated generally at 100. Specifically, system 100 is configured to transfer power through the skin 102 of a subject (e.g., a patient) to supply power to an implanted medical device (not shown). System 100 may be used to transfer alternating current (AC) or direct current (DC) power, depending on the desired application. In this embodiment, system 100 includes an external connector 104 electrically couple-able to an internal connector 106. Internal connector 106 is positioned within the body of the patient, and external connector 104 is positioned outside of the body. In the embodiment shown in FIG. 1, internal connector 106 is located subcutaneously. Alternatively, depending on the application, internal connector 106 may be located deeper within the body. In various embodiments, internal connector 106 is configured to be positioned within the abdominal cavity of the subject. Internal connector 106 may be hermetically sealed and formed of corrosion-resistant materials to enable placement within the body. In various embodiments, internal connector 106 is positioned adjacent to and/or anchored to a bone (e.g. a rib).

External connector 104 includes a microneedle array 110 for electrically and physically coupling to internal connector 106. Specifically, microneedle array 110 includes a plurality of electrically conductive microneedles 112. Each microneedle 112 includes a rigid or semi-rigid conductive core material coated with an insulation material (e.g., Tefzel ETFE). The conductive core material is exposed at a tip of microneedle 112. For example, each microneedle 112 may include a metal alloy coated with a thin polymer insulation material. In this embodiment, microneedles 112 are evenly spaced from one another, and may be arranged in a one-dimensional array (i.e., spaced along a line) or a two-dimensional grid. Microneedles 112 include a positive set of microneedles and a negative set of microneedles. To couple to internal connector 106, microneedles 112 pierce skin 102 (e.g., passing through pores in skin 102).

In various respects, the term "microneedle" refers to a thin-diameter or needle-like structure with a conductive element, and in certain respects a conductive structure configured for piercing tissue or the skin. One of skill will appreciate from the description herein that a variety of assemblies may be used to form the microneedles depending on the application. For example, the conductive microneedles may be formed entirely of conductive materials. In another example, the microneedle includes an insulative body and a conductive element. The microneedle may be formed of an insulator hollow body loaded with a conductive material. Other structures will be further understood from the following description.

Further, internal connector 106 includes a microwire holder 114 that has a plurality of electrical contacts 116. Electrical contacts 116 include a positive set of electrical contacts and a negative set of electrical contacts. To transfer power, external connector 104 is positioned relative to internal connector 106 such that microneedles 112 extend through the skin 102 and engage electrical contacts 116, electrically coupling external connector 104 to internal connector 106. Specifically, external connector 104 is positioned such that the positive set of microneedles engages the positive set of electrical contacts and the negative set of microneedles engages the negative set of electrical contacts.

In an alternative embodiment, external connector 104 includes microwire holder 114 and internal connector 106 includes microneedle array 110. Accordingly, instead of extending from the outside of a subject's body to the inside of the subject's body, microneedles 112 extend from the inside of the subject's body to the outside of the subject's body. In such an embodiment, microwire holder 114 is external to the subject's body (instead of subcutaneous), and receives microneedles 112 extending from internal connector 106.

In this embodiment, system 100 further includes a power cable 120 that supplies power to external connector 104 from an external power source (not shown). The power source may include external batteries, AC mains, or an external controller. Power cable 120 includes a plug 122 that engages an electrical socket 124 on external connector 104. In some embodiments, plug 122 magnetically couples to electrical socket 124. Accordingly, when a sufficient force is exerted on power cable 120, plug 122 disengages from electrical socket 124 without pulling external connector 104 away from internal connector 106.

As shown in FIG. 1, internal connector 106 is electrically coupled to an internal power cable 126. Internal power cable 126 may power from internal connector 106 to, for example, an implanted medical device and/or an implanted battery. Implanted medical device may be any medical device capable of receiving power using system 100. For example, implanted medical device may be a pacemaker, a ventricular assist device (VAD), a spinal cord stimulation (SCS) device, or a deep brain stimulation (DBS) device.

In this embodiment, internal connector 106 includes an anchor 130 for securing the position of internal connector 106 within the body. For example, as will be appreciated by those of skill in the art, anchor 130 may anchor internal connector 104 to a bone (e.g., a rib) of the subject. Alternatively, anchor 130 may be any suitable anchoring device. For example, anchor 130 may be implemented using nitinol hooks or sutures that engage tissue of the subject. Further, tissue ingrowth around internal connector 106 may be used to anchor internal connector 106. One will appreciate that internal connector 106 may include a variety of tissue or skin anchors 130 depending on the application. In various embodiments, internal connector 106 is anchored to a bone. The optional anchoring may be used to mitigate the risk of migration of internal connector 106 over time. External connector 104 and internal connector 106 may be left in place for a relatively long period of time and/or may be replaced periodically. In such cases, there may be the possibility that internal connector 106 moves from its implant location and makes it harder for internal connector 106 to be located and/or accessed. If internal connector 106 migrates too much, there may also be the risk of the connection to external connector 104 becoming loose. In certain applications and implant locations, however, the risk of migration is relatively low and tolerable even without anchoring structures. In some embodiments, external connector 104 and/or internal connector 106 may include safety mechanisms to prevent an overcurrent condition if external connector 104 and/or internal connector 106 are incorrectly connected to one another.

Figure 2:
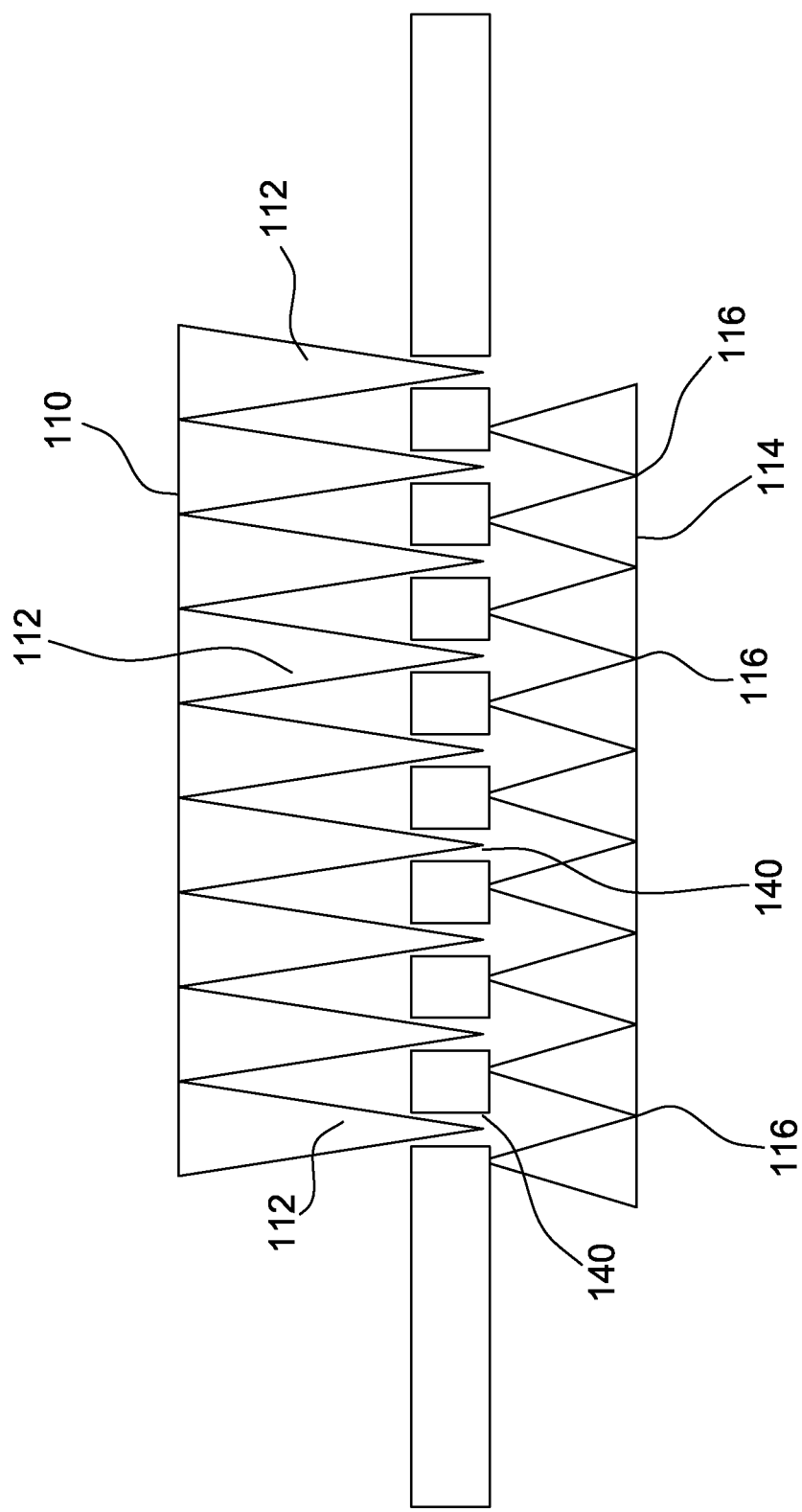
FIG. 2 is a schematic diagram of a microneedle array and a microwire holder that may be used with the transcutaneous power transfer system shown in FIG. 1.

FIG. 2 is a schematic diagram of microneedle array 110 and microwire holder 114 that may be used with the transcutaneous power transfer system shown in FIG. 1. In this embodiment, each microneedle 112 includes a rigid or semi-rigid conductive core material coated with an insulation material (e.g., Tefzel ETFE). The conductive core material is exposed at a tip 140 of microneedle 112. For example, each microneedle 112 may include a metal alloy coated with a thin polymer insulation material. Alternatively, any materials may be used that enable microneedle array 110 to function as described herein. In some embodiments, microneedles 112 have an anti-bacterial coating and/or an anti-corrosive coating. In various embodiments, microneedles 112 include a corrosion-resistant material such as MP35N, titanium, DFT® sold by Fort Wayne Metals, Pt—Ir, and the like. In various embodiments, microneedles 112 are formed of an outer body of corrosion-resistant material and/or biologically-compatible material as understood by one of skill.

As shown in FIG. 2, in this exemplary embodiment, both microneedle array 110 and microwire holder 114 have a sawtooth configuration. Accordingly, when coupling microneedle array 110 to microwire holder 114, microneedles 112 are guided into and automatically aligned with microwire holder 114 to electrically couple to electrical contacts 116. This allows the subject or another individual (e.g., a physician) to successfully couple microneedle array 110 to microwire holder 114 relatively easily. One will appreciate from the description herein other structures for guiding microneedle array 110 into connection with internal connector 106. Other examples include rails, pins, and similar mechanical guides. In various embodiments, at least one of microneedle array 110 and internal connector 106 includes magnets (e.g. permanent and/or electromagnets) for guiding them into proper alignment. In the case of use of magnets, system 100 may include a mechanism for sensing when the magnets are in contact. In various embodiments, system 100 includes a resistor for detecting when microneedle array 110 and internal connector 106 have formed a proper connection. System 100 can thus generate a signal to indicate to a user whether a proper connection has been formed or not. In various embodiments, system 100 includes a mechanism for signaling to a user whether a proper connection has been made. The signal may be visual, audible, or tactile (e.g., internal connector 106 may vibrate). System 100 may be configured to generate a signal indicative of whether proper connection has been made. The signal may be transmitted to another component (e.g., a controller). In response, the controller or other component may generate an alarm if an improper connection occurs. The controller may enter a unique mode, such as a low power state or auto shutoff to avoid further consequence. In one embodiment, when an improper connection occurs, power is switched from an external power source to an internal power source.

In some embodiments, external connector 104 is easily detachable from internal connector 106. Further, external connector 104 and/or internal connector 106 may include safety mechanisms to prevent an overcurrent condition if external connector 104 and internal connector 106 are incorrectly connected to one another.

For example, in some embodiments, an external power source (not shown in FIGS. 1 and 2) includes an overcurrent detector that includes a resistor (e.g., of approximately 0.1 Ohm) in series with the external power source. A differential amplifier may be used to detect the voltage drop across the resistor, and if the voltage drop exceeds a predetermined threshold (e.g., 100 mV), a solid state switch may be used to switch off or limit the current delivered by the external power source. In the event of an overcurrent condition, an alarm or other alert may be generated directly by the external power source and/or transmitted to a remote computing device (e.g., a smartphone, tablet, etc.) to notify the subject and/or physician of the overcurrent condition.

In some embodiments, the safety mechanism includes fuse circuitry that breaks when an overcurrent condition occurs. Specifically, the fuse circuitry measures a total resistance between a positive end and a negative end of the fuse circuitry. If the measured total resistance is below a first predetermined threshold, the circuit breaks (e.g., short circuits). Further, if the measured total resistance is greater than a second predetermined threshold, a loose connection/disconnection alert is generated. This fuse circuitry may be located, for example, outside of the subject (e.g., within power cable 120), and may be powered by an external power source. Alternatively, the fuse circuitry may be located within the subject, and may be powered by a subcutaneous device battery.

In some embodiments, the safety mechanism includes an analog switch for each electrical contact 116. For example, each analog switch could be coupled to a resistor (e.g., of approximately 0.1 Ohm). If there is an overcurrent and/or a voltage drop exceeding a predetermined threshold (e.g., 100 mV) for only a few electrical contacts 116 (e.g., one or two electrical contacts 116), those electrical contacts 116 can be switched off, allowing the remaining electrical contacts 116 to continue supplying power to the implanted device. However, if more electrical contacts 116 demonstrate an overcurrent and/or a voltage drop exceeding the predetermined threshold, power may be disconnected completely.

By using microneedle array 110 and microwire holder 114, system 100 prevents overheating at the connection between external connector 104 and internal connector 106. Heating occurs due to the flow of current through resistive wires. The flow of current produces generation of power (i.e., $P=I^2R$) which subsequently results in a temperature rise. As temperature increases, power dissipation by convention, conduction, and radiation also increases. Equilibrium is reached when power generation equals power dissipation. Assuming that radiation is the only source of power dissipation, the rise in temperature for current I is given by:

$$\Delta T = \frac{I^2 \rho}{\epsilon \sigma T_R^3 \pi^2} \frac{l}{d^3 n^2}$$

where $\rho$ is the resistivity of the material, l is the length of the wire, d is the diameter of the wire, n is the number of wires in the connector, $\sigma$ is the Stefan-boltzman constant, $T_R=300K$ is the room temperature, and $\epsilon$ is emissivity.

An exemplary VAD may require approximately 7 Watts of power at 12 Volts, which results in a current flow of 0.583 Amps. This gives n=307 for a $\Delta T=0.1$ C using copper wire ($\rho=1.68$ e−8 $\Omega$m, $\epsilon=0.04$) with d=10 μm and l=1 mm. As the radiation is taken as the only mechanism of power dissipation, n=307 should result in an even lower change in temperature. Further, d up to 40 μm (skin pore size is approximately 50 μm) may be used if needed. Also, using oxidation, the emissivity of copper can be increased to 0.8 if needed. If both of these adjustments are made together, n=1 (i.e., a single microneedle 112) results in a temperature rise of 0.1 C. Notably, these figures may be conservative examples, as they only consider radiation as a heat dissipation mechanism. Accordingly, fewer microneedles 112 could likely be used. The above specifications are representative only. One of skill in the art will appreciate that the specifications of system 100 may vary depending on the desired application.

Figure 3:
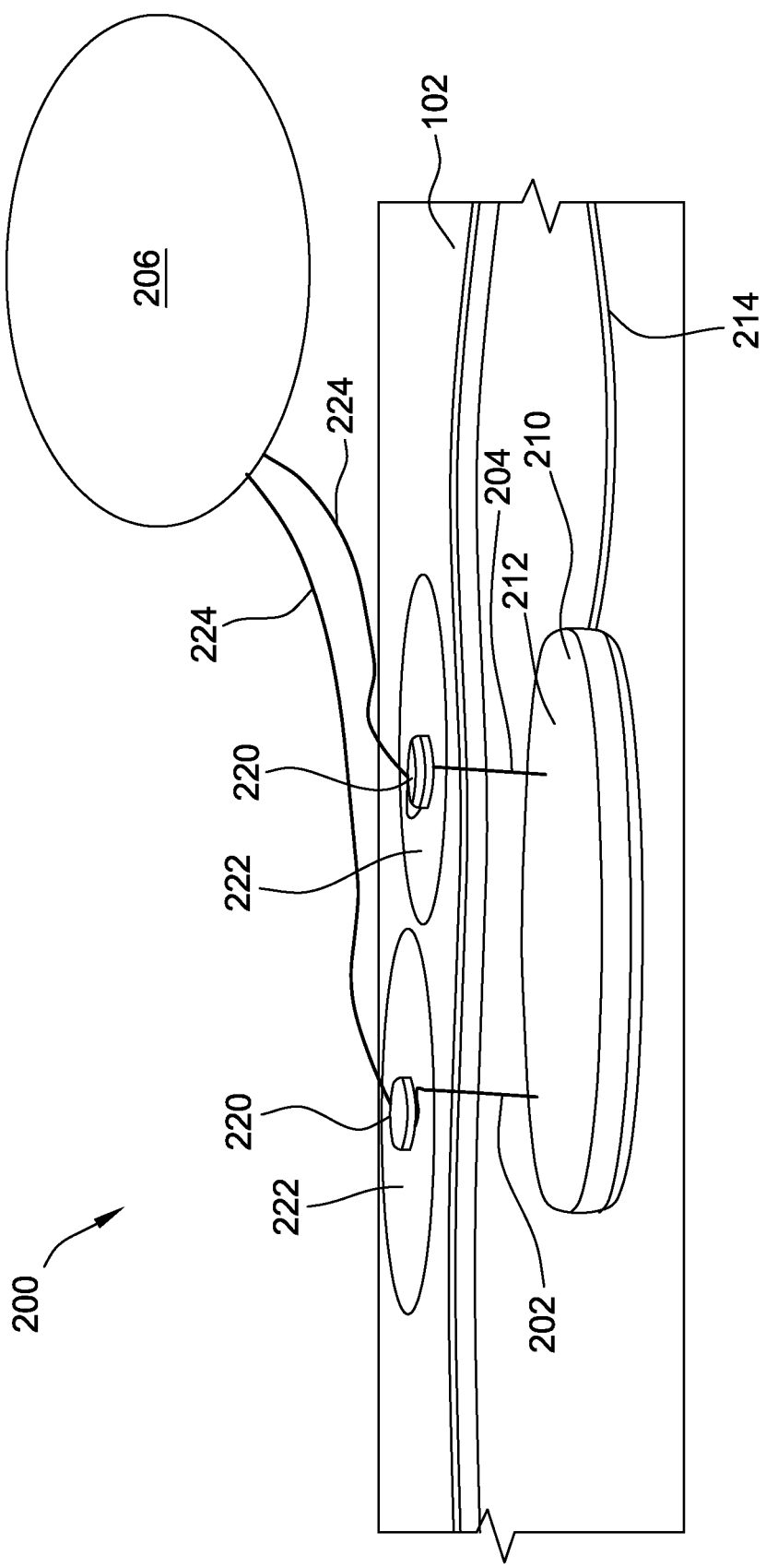
FIG. 3 is a schematic diagram of another embodiment of a transcutaneous power transfer system.

FIG. 3 is a schematic diagram of another embodiment of a transcutaneous power transfer system 200. Instead of a microneedle array, system 200 includes at least one positive microconductor 202 and at least one negative microconductor 204 that extend through the skin 102. In FIG. 3, one positive microconductor 202 and one negative microconductor 204 are shown. However, those of skill in the art will appreciate that system 200 may include multiple positive microconductors 202 and multiple negative microconductors 204 (e.g., for redundancy purposes). Positive and negative microconductors 202 and 204 are conductive components that conduct AC and/or DC power generated by an external power source 206. Positive and negative microconductors 202 and 204 may each be, for example, a cable having a first electrical terminal and a second electrical terminal at opposite ends of the cable, as described below in association with FIG. 4. External power source 206 may be, for example, a battery pack capable of supplying approximately 12-14 Volts at 0.76 Amps. Alternatively, external power source 206 may be any suitable power source.

System 200 further includes a control unit 210 implanted in the subject. Control unit 210 may be subdermally implanted (e.g., embedded in a subcutaneous fat layer), or may be implanted deeper within patient. Control unit 210 includes a housing 212 that encloses a plurality of electronic components, as described in detail in association with FIG. 7. Control unit 210 receives power from positive and negative microconductors 202 and 204, and supplies power to an implanted device (not shown) via a driveline 214. Specifically, control unit 210 includes positive and negative electrical contacts (not shown in FIG. 3) that electrically couple to positive and negative microconductors 202 and 204, respectively. Driveline 214 may be, for example, a driveline cable as described in U.S. Patent Application Publication No. 2016/0064117 filed Sep. 3, 2015, which is hereby incorporated by reference in its entirety for all purposes. Driveline 214 may provide DC power, bi-phasic power, or tri-phasic power to the implanted device in accordance with the power requirements of the implanted device. For example, if the implanted device includes a brushless DC motor, driveline 214 may carry DC power.

In some embodiments, control unit 210 may be external to the subject's body (i.e., not subcutaneously implanted). In such embodiments, driveline 214 may extend through skin 102 (e.g., using a connector assembly similar to that shown in FIGS. 1 and 2) and may directly power the implanted device.

In this embodiment, positive and negative microconductors 202 and 204 are each electrically coupled to a detachable button 220 adhered to skin 102 using a protective barrier 222. Further, each button 220 is electrically coupled to external power source 206 via a power cable 224. Protective barrier 222 may be, for example, an adhesive tape barrier. When a sufficient force is exerted on power cables 224, buttons 220 detach from skin 102 and positive microconductors 202 and 204 to prevent injury to the subject.

FIG. 4 is a schematic diagram of a microconductor 400 that may be used with system 200 (shown in FIG. 3). For example, microconductor 400 may be positive microconductor 202 or negative microconductor 204 (shown in FIG. 3). As shown in FIG. 4, microconductor 400 includes a cable 402 having a first electrical terminal 404 and a second electrical terminal 406 at opposite ends of cable 402. In this embodiment, cable 402 includes a rigid or semi-rigid conductive core material coated with an insulation material. For example, cable 402 may be a Tefzel coated cable having a diameter of approximately 0.0085 inches. Alternatively, cable 402 may have any composition and dimensions that enable microconductor 400 to function as described herein. In some embodiments, microconductor 400 has an antibacterial coating and/or an anti-corrosive coating. In some embodiments, cable 402 may be made of 7 or 19 strands of MP35N, each strand having a core of silver to enhance the overall conductivity of cable 402. Further, a display end of cable 402 may be made entirely of silver because of silver's high conductivity and antimicrobial properties. In some embodiments, the Tefzel insulation on cable 402 may include a thin outer layer of Tefzel embedded with nanoparticles of silver that impart antimicrobial properties to cable 402.

First electrical terminal 404 contacts the positive electrical contact of control unit 210 to electrically couple microconductor 400 to control unit 210. As shown in FIG. 4, first electrical terminal 404 has a pointed profile to facilitate piercing skin 102 and piercing housing 212, as described in detail below. Second electrical terminal 406 electrically couples microconductor 400 to button 220 in this embodiment. Further description of exemplary materials and structures for a VAD-based system in connection with the embodiments described herein may be understood from U.S. Pub. No. 2016/0064117, which is hereby incorporated by reference in its entirety for all purposes.

FIG. 5 is a schematic diagram of an injection tool 500 that may be used to implant exemplary microconductor 400. Injection tool 500 includes a hollow injector barrel 502 that receives microconductor 400. Injector barrel 502 may have, for example, a diameter of approximately 0.01625 inches (i.e., equivalent to a 27 gauge needle). Injection tool 500 also includes a handle 504 that enables a user (e.g., a physician) to hold and guide injection tool 500 when implanting microconductor 400.

FIG. 6 is a schematic diagram of microconductor 400 loaded into injection tool 500. To implant microconductor 400, a user (e.g., a physician) maneuvers injection tool 500 such that first electrical terminal 404 pierces skin 102. The user further maneuvers injection tool 500 to ensure first electrical terminal 404 pierces housing 212 and contacts the positive electrical contact of control unit 210. Once microconductor 400 is successfully electrically coupled to control unit 210, the user withdraws injection tool 500, leaving microconductor 400.

Figure 7:
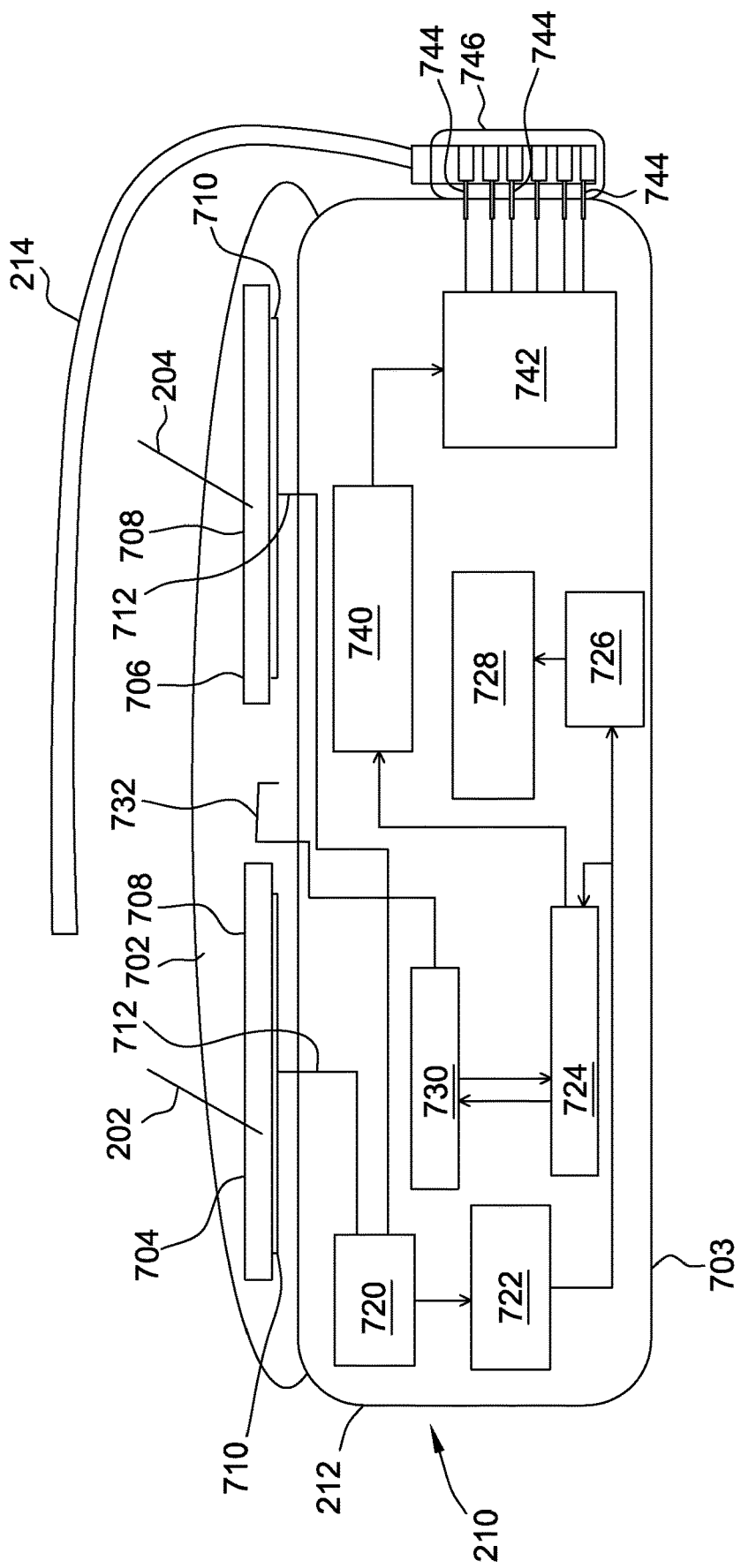
FIG. 7 is a schematic diagram of a control unit that may be used with the transcutaneous power transfer system shown in FIG. 3.

FIG. 7 is a schematic diagram of control unit 210. As shown in FIG. 7, housing 212 includes a self-healing septum 702 attached to a metallic (e.g., titanium) case 703. Specifically, septum 702 is able to be pierced (i.e., by first electrical terminal 404) and them reform around the object that did the piercing. Septum 702 may be made of, for example, silicone or any other suitable material (e.g., hydrophobic polymer materials). In this embodiment, a positive electrical contact 704 and a negative electrical contact 706 are embedded within septum 702. Positive electrical contact 704 receives and electrically couples to positive microconductor 202, and negative electrical contact 706 receives and electrically couples to negative microconductor 204.

In this embodiment, positive and negative electrical contacts 704 and 706 each include a metallic mesh 708 (e.g., titanium wool) or highly conductive silicone that is doped with microparticles of metallic silver. Accordingly, positive and negative microconductors 202 and 204 need only contact a portion of the metallic mesh or conductive silicone, as opposed to a discrete electrical contact. This improves ease of implantation and operation of system 200. Each metallic mesh 708 is sintered to a metallic (e.g., titanium) plate 710, which is in turn connected to a feedthrough 712 for electrically coupling to electrical components inside control unit 210. Similarly, in embodiments with conductive silicone, the conductive silicone may be adhered to a metallic (e.g., silver) plate that is in turn connected to a feedthrough for electrically coupling to electrical components inside control unit.

In this embodiment, microconductors 202 and 204 are electrically coupled to a full wave bridge rectifier 720 that receives AC power from positive and negative microconductors 202 and 204 and converts it to DC power for use by control unit 210. This approach simplifies connection of the power source, because when microconductors 202 and 204 conduct AC power, microconductors 202 and 204 may be inserted positive and negative electrical contacts 704 and 706 without any concern about the polarity. Alternatively, as noted above, control unit 210 may receive DC power from positive and negative microconductors 202 and 204. The DC power is regulated using power conditioning circuitry 722 and provided to a microprocessor 724 that controls operation of control unit 210. In this embodiment, power conditioning circuitry also provides power to recharge circuitry 726 for charging a battery 728 within control unit 210. If control unit 210 stops receiving power from external power source 206, battery 728 may temporarily provide power to control unit 210 and the implanted device. Battery 728 may be, for example, a lithium ion battery having a nominal voltage of 3.2 V and a rated capacity of 1150 milliampere hours (mAh). Alternatively, battery 728 may have any specifications that enable control unit 210 to function as described herein. In some embodiments, control unit 210 may not include recharge circuitry 726 and battery 728.

Microprocessor 724 is communicatively coupled to a Bluetooth low energy (BLE) transceiver 730. Using an antenna 732, BLE transceiver 730 is capable of transmitting and receiving signals from a remote device (e.g., an external programmer). For example, antenna 732 may transmit signals to a remote device (e.g., a mobile computing device, a smartphone, a tablet, etc.) to notify the subject and/or physician of problems associated with operation of the implanted device and/or control unit 210 (e.g., cavitation, suction, arrhythmia, excessive pump loading, failure of battery 728, low power from external power source 206, intermittent connectivity with/disconnection from positive and negative microconductors 202 and 204, etc.). For example, antenna 732 may transmit signals to a remote device when an overcurrent condition is detected or fuse circuitry breaks, as described above. The remote device may include a patient's personal smartphone. Further, the remote device may include an application that communications with the patient directly and that communicates with a remote data management system that provides data to health care management personnel and/or a physician to aide in management of the implanted device.

Alternatively, microprocessor 724 may communicate with remote devices using any suitable communications scheme. For example, in some embodiments, microprocessor 724 may communicate conductively (e.g., using amplitude or frequency modulated signals) through microconductors 202 and 204. Further, in some embodiments, driveline 214 may transmit a communication signal (e.g., encoded as an amplitude or frequency modulated signal) on top of the power signal.

Microprocessor 724 is also communicatively coupled to a motor microcontroller 740. Motor microcontroller 740 controls operation of the implanted device (e.g., a VAD, SCS device, and/or DBS device) based on control signals received from microprocessor 724. Specifically, motor microcontroller 740 causes a motor driver 742 to transmit control signals to the implanted device through driveline 214. Driveline 214 also provides power to the implanted device. In this embodiment, motor driver 742 is communicatively coupled to driveline 214 via a plurality of driveline feedthroughs 744 and a driveline connector 746, as shown in FIG. 7. In various embodiments, a microcontroller is disposed on-board the implanted medical device (e.g. VAD or pacemaker) or in a hermetic housing separate from control unit 210.

In system 200, control unit 210 is capable of detecting that at least one of positive and negative microconductors 202 and 204 has become disconnected from positive and negative electrical contacts 704 and 706. For example, in one embodiment, power conditioning circuit 722 may include a voltage detection circuit that detects a voltage level delivered by external power source 206. When the voltage drops below a predetermined level, either due to a disconnection or because a battery of external power source 206 has become sufficiently discharged to warrant replacement/recharging, an alert for the patient and/or healthcare provider maybe generated and transmitted using BLE transceiver 730. The voltage level delivered by external power source 206 may be measured by microprocessor 724 using an integral A/D converter. Alternatively, external power source 206 may monitor a voltage drop across a resistor (e.g., 0.1 ohm) in series with external power source 206 to detect when the voltage drop is too low (thus indicating that delivered current is too low or zero).

Further, as described above, safety mechanisms to detect a disconnection may include an overcurrent detector in series with external power source 206, fuse circuitry that breaks when an overcurrent condition occurs, and/or analog switches for each electrical contact point. In response to detecting a disconnection, control unit 210 generates an alert. For example, in one embodiment, control unit 210 generates an audible alert. In another embodiment, control unit 210 vibrates. In yet another embodiment, BLE transceiver 730 causes antenna 732 to transmit an alert signal. Alternatively, control unit 210 may generate any suitable alert. Furthermore, a smartphone or other mobile computing device that receives an alert may transmit the alert to a device management center. The smartphone or other mobile computing device may have an application that instructs the patient how to manage the implanted device (e.g., instructing the patient to replace external power source 206, or to replace microconductors 202 and 204 when a voltage of external power source 206 remains high but a voltage at power conditioning circuit 722 is excessively low. Of course, if system 200 shows signs of failure or malfunction, both the patient and professionals helping the patient manage the implanted device will be notified.

In various embodiments, system 200 includes a resistor for detecting when positive and negative microconductors 202 and 204 and positive and negative electrical contacts 704 and 706 have formed a proper connection. System 200 can thus generate a signal to indicate to a user whether a proper connection has been formed or not. In various embodiments, system 200 includes a mechanism for signaling to a user whether a proper connection has been made. The signal may be visual, audible, or tactile (e.g., control unit 210 may vibrate). System 200 may be configured to generate a signal indicative of whether proper connection has been made. The signal may be transmitted to another component (e.g., a controller). In response, the controller or other component may generate an alarm if an improper connection occurs. The controller may enter a unique mode, such as a low power state or auto shutoff to avoid further consequence. In one embodiment, when an improper connection occurs, power is switched from an external power source to an internal power source.

Figure 8:
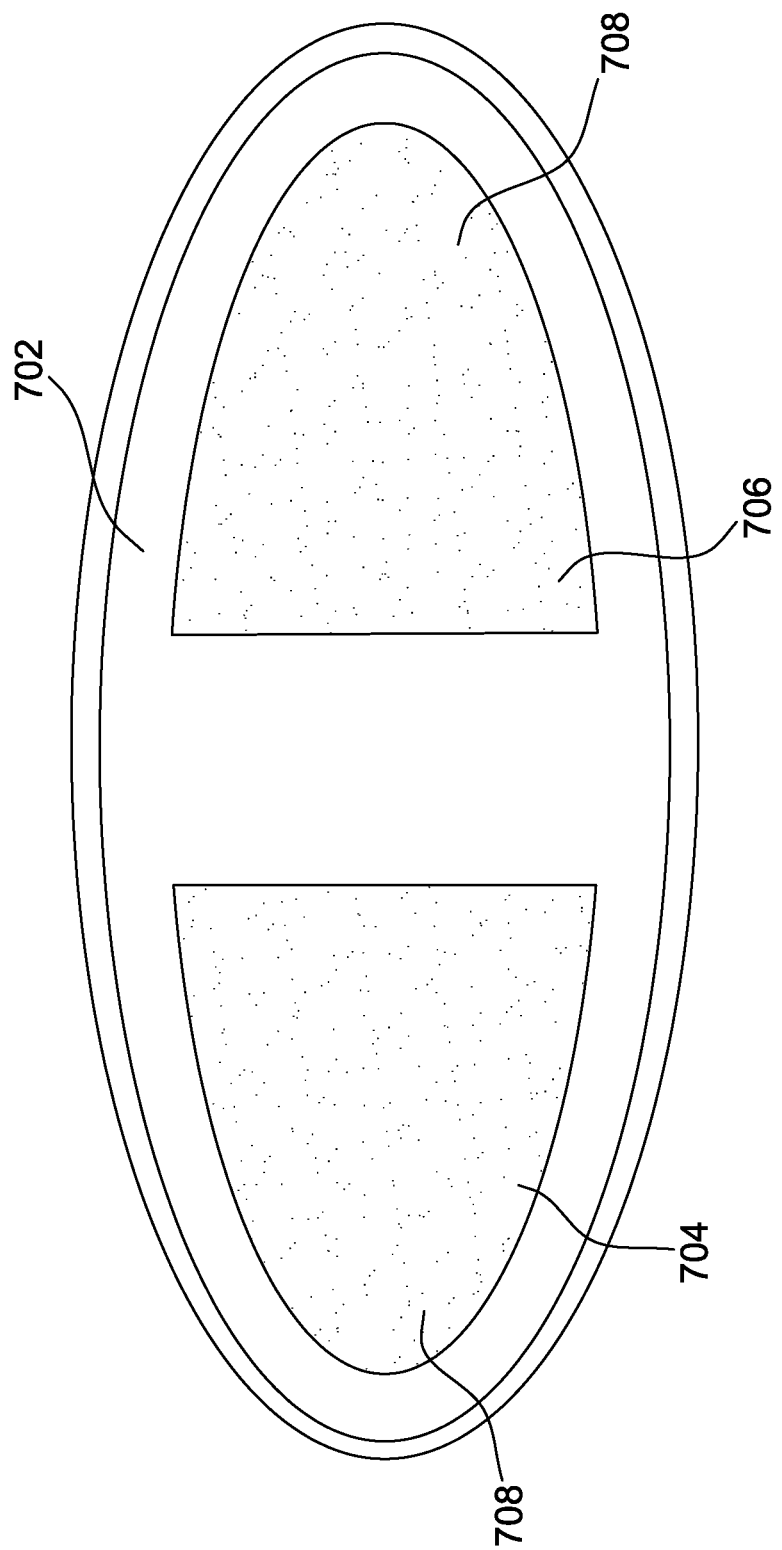
FIG. 8 is a schematic diagram of a portion of the control unit shown in FIG. 7.

FIG. 8 is a schematic diagram of a portion of control unit 210. Specifically, FIG. 8 shows positive and negative electrical contacts 704 and 706 implemented as metallic mesh 708 embedded within septum 702. As described above, metallic mesh 708 may be, for example, titanium wool.

Figure 9:
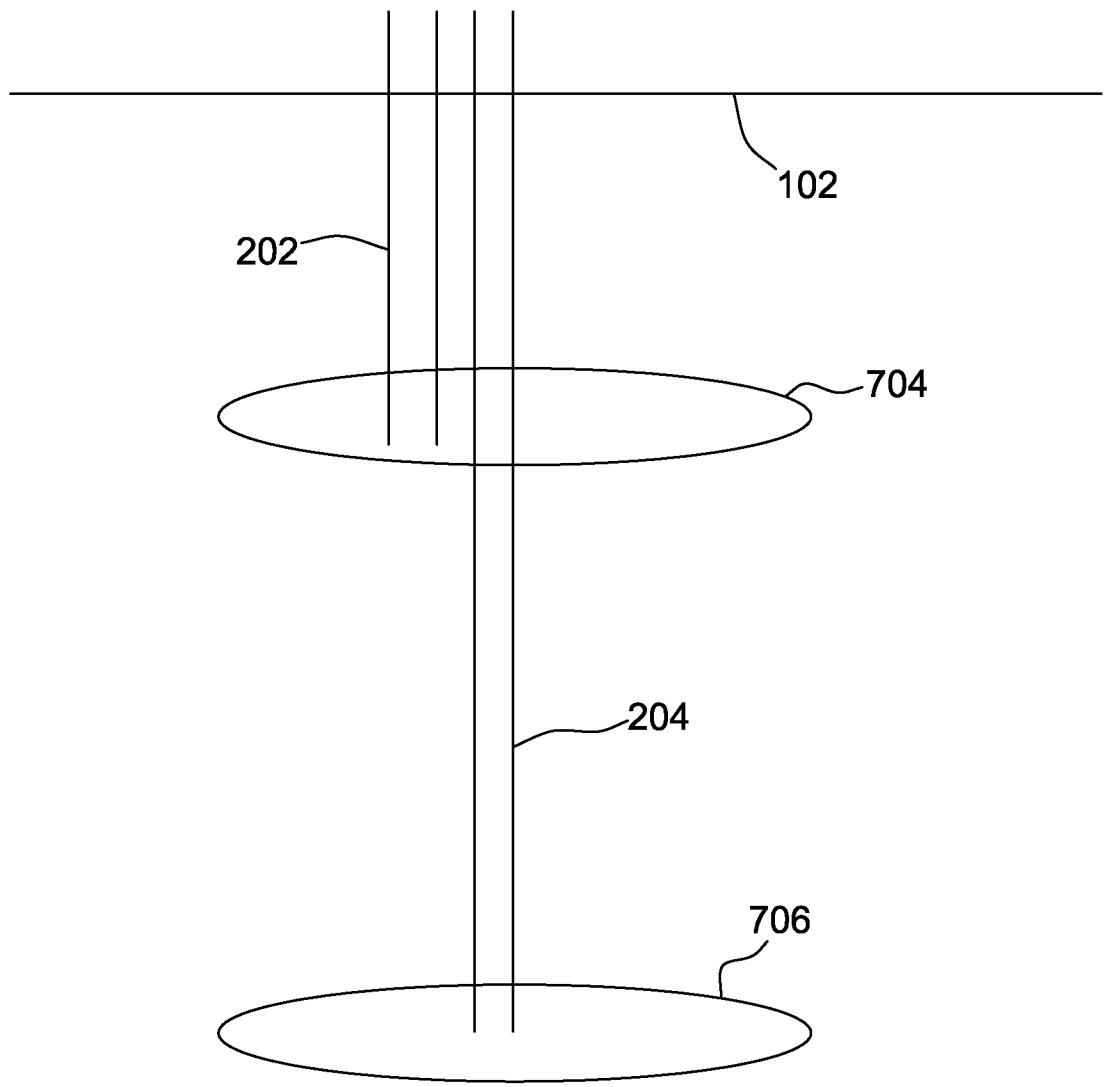
FIG. 9 is a schematic diagram of one configuration of a positive microconductor, a negative microconductor, a positive electrical contact, and a negative electrical contact that may be used with the transcutaneous power transfer system shown in FIG. 3.

In the embodiment of FIGS. 7 and 8, positive and negative electrical contacts 704 and 706 are located side by side (relative to skin 102). Alternatively, positive and negative electrical contacts 704 and 706 may be located in different orientations with respect to one another. For example, FIG. 9 is a schematic diagram of an alternative configuration of positive and negative electrical contacts 704 and 706. In the embodiment of FIG. 9, positive electrical contact 704 is positioned above negative electrical contact 706. Those of skill will appreciate that alternatively, negative electrical contact 706 may be positioned above positive electrical contact 704. That is, positive electrical contact 704 is located closer to skin 102 than negative electrical contact 706. As before, positive and negative electrical contacts 704 and 706 are located within septum 702, but septum is omitted from FIG. 9 for clarity.

Figure 10:
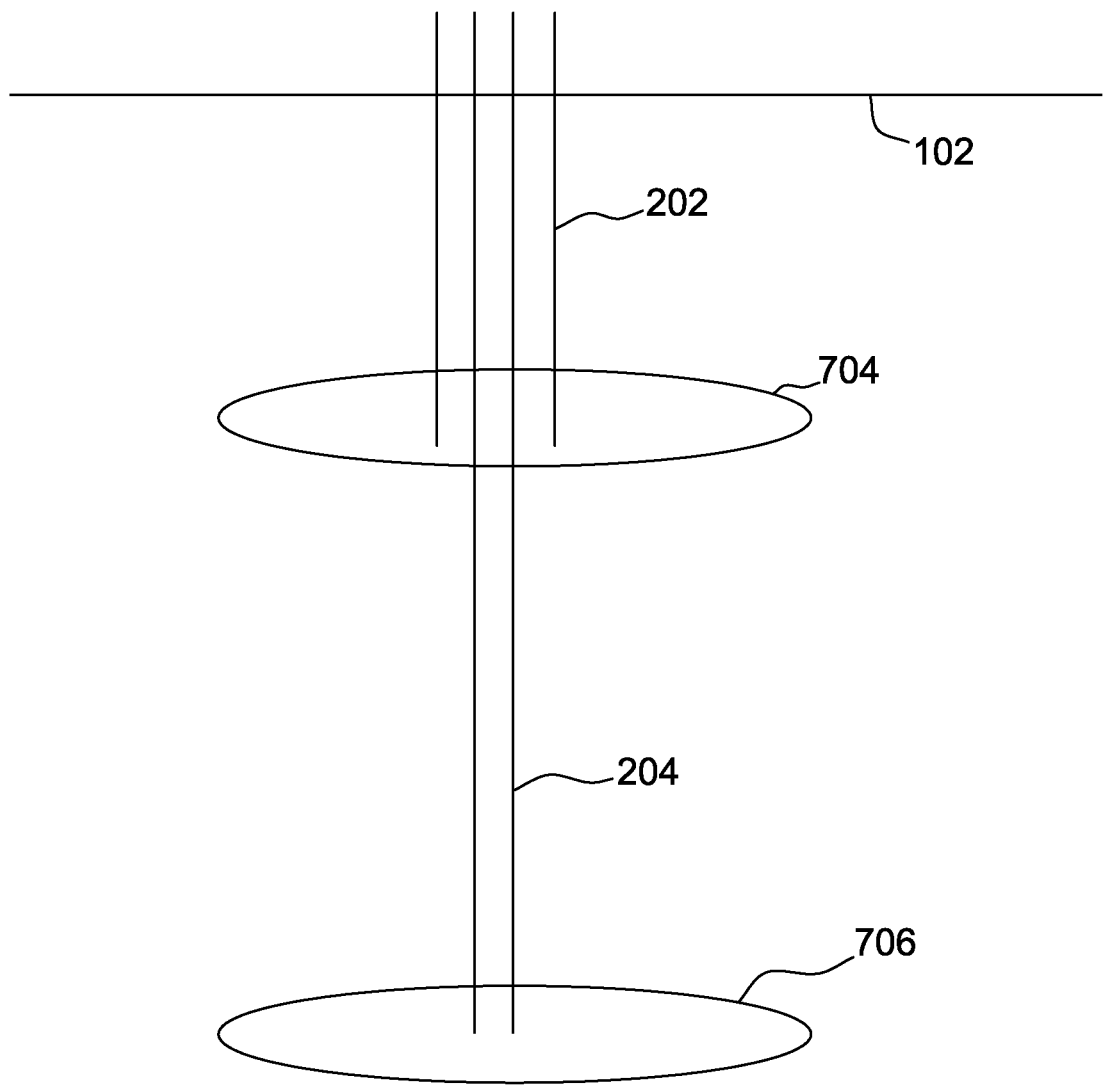
FIG. 10 is a schematic diagram of another configuration of a positive microconductor, a negative microconductor, a positive electrical contact, and a negative electrical contact that may be used with the transcutaneous power transfer system shown in FIG. 3.

FIG. 10 is a schematic diagram of another alternative configuration. In the embodiment of FIG. 10, similar to the embodiment of FIG. 9, positive electrical contact 704 is positioned above negative electrical contact 706. However, unlike the embodiment of FIG. 9, positive and negative microconductors 202 and 204 are coaxial with one another. Specifically, positive microconductor 202 circumscribes a segment of negative microconductor 204 that extends between skin 102 and positive electrical contact 704. After positive microconductor 202 terminates, negative microconductor 204 extends until it reaches negative electrical contact 706. Having positive and negative microconductors 202 and 204 coaxial with one another may improve the ease of implantation of system 200. For example, in such embodiments, positive and negative microconductors 202 and 204 may be implanted at the same time using the same injection tool (e.g., similar to injection tool 500).

The systems and methods described herein may be used to provide power to any suitable implanted device. For example, the systems and methods described herein may be used in conjunction with devices and systems described in U.S. Patent Publication No. 2015/0290374 filed Apr. 15, 2015, U.S. Patent Publication No. 2015/0290378 filed Apr. 15, 2015, U.S. Pat. No. 6,100,618 filed Oct. 1, 1997, U.S. Pat. No. 6,365,996 filed Feb. 10, 1998, U.S. Pat. No. 5,708,346 filed Jun. 11, 1996, U.S. Pat. No. 8,562,508 filed Dec. 30, 2009, U.S. Pat. No. 8,794,989 filed Dec. 8, 2011, U.S. Pat. No. 8,858,416 filed Aug. 26, 2013, and U.S. Pat. No. 8,682,431 filed Jan. 23, 2013, all of which are hereby incorporated by reference in their entirety.

Figure 11:
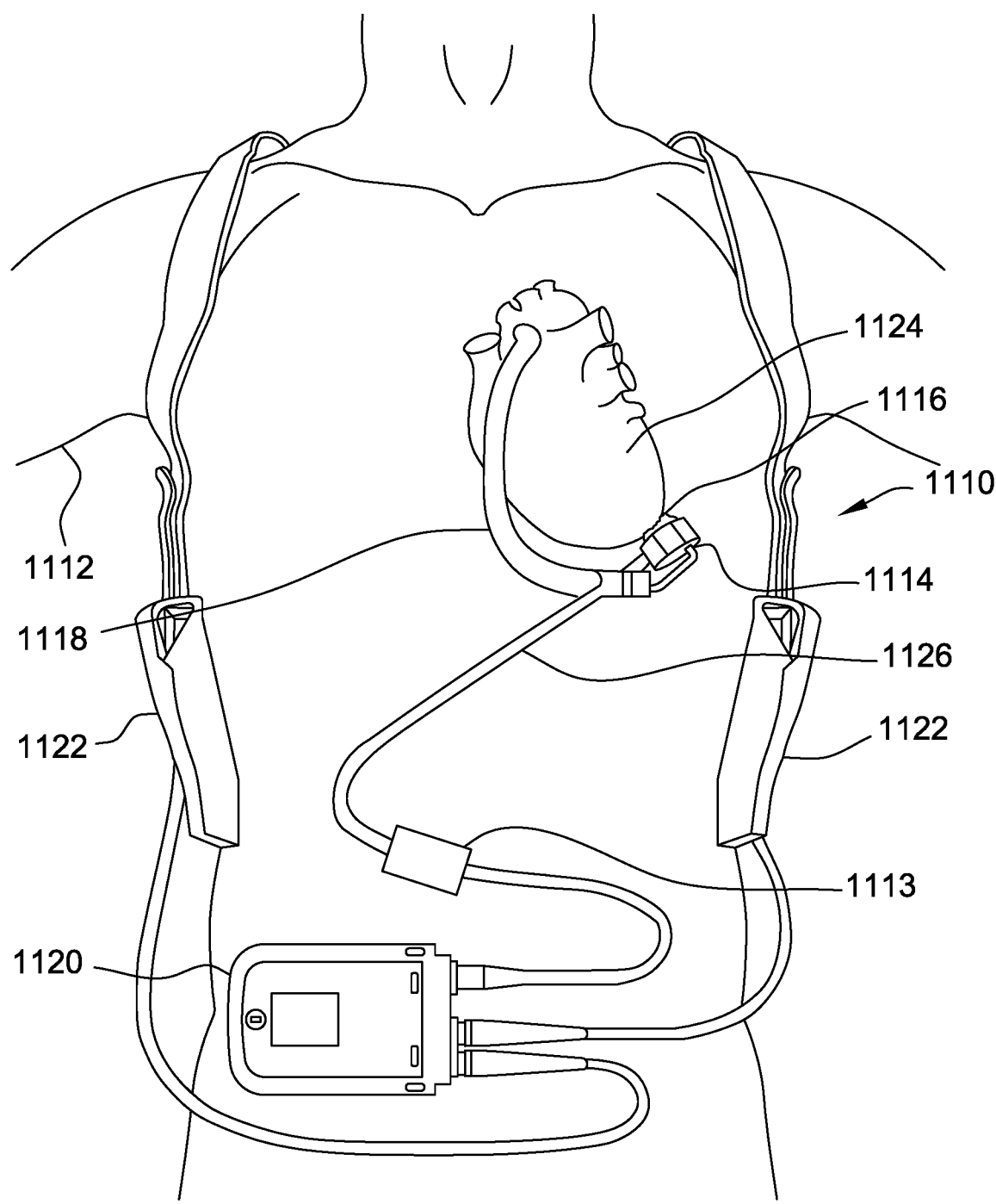
FIG. 11 is a schematic diagram of a mechanical circulatory support system implanted in a subject's body that may be used with the systems shown in FIG. 1 and FIG. 3.

As an Example, FIG. 11 is a schematic diagram of an exemplary mechanical circulatory support system 1110 implanted in a subject's body 1112. System 1110 includes a transcutaneous connector 1113 similar to those described above. In various embodiments, connector 1113 is implemented using components of system 100 (shown in FIG. 1) and/or system 200 (shown in FIG. 3). Alternatively, connector 1113 may include any components that enable system 1110 as would be understood by one of skill from the description herein. Further, connector 1113 is not limited to being used with mechanical circulatory support system 1110, but may be used in any system in which power is supplied transcutaneously to an implanted device.

Mechanical circulatory support system 1110 includes an implantable blood pump 1114, ventricular cuff 1116, outflow cannula 1118, system controller 1120, and power sources 1122. One or more components of system controller 1120 and/or power sources 1122 may be implanted within the subject instead of external to the subject as shown in FIG. 11. Implantable blood pump 1114 may include a VAD that is attached to an apex of the left ventricle, as illustrated, or the right ventricle, or both ventricles of the heart 1124. The VAD may include a centrifugal (as shown) or axial flow pump capable of pumping the entire output delivered to the left ventricle from the pulmonary circulation (i.e., up to 10 liters per minute). Related blood pumps applicable to the systems and methods described herein are described in greater detail in U.S. Pat. Nos. 5,695,471, 6,071,093, 6,116, 862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIG. 11, blood pump 1114 may be attached to the heart 1124 via the ventricular cuff 1116 which is sewn to heart 1124 and coupled to blood pump 1114. The other end of blood pump 1114 connects to the ascending aorta via outflow cannula 1118 so that the VAD effectively diverts blood from the weakened ventricle and propels it to the aorta for circulation to the rest of the patient's vascular system.

In various embodiments, mechanical circulatory support system 1110 is configured for a temporary support mode. In an exemplary embodiment, mechanical circulatory support system 1110 is configured to enable a free mode whereby the patient can be supported for a time free from the external components. Batteries 1122 and control circuitry can be implanted to operate the pump. Connector 1113 facilitates easy disconnection (and reconnection) of the external components. In normal usage, a driveline 1126 is connected through connector 1113. Blood pump 1114 is powered by main batteries or another power source outside body 1112. To convert to free mode, the external portion of driveline 1126 is removed from connector 1113. System 1110 recognizes the disconnection and converts to the free mode by operating using the implanted power source. In some embodiments, the control circuitry includes a state detection module and selects a state based on whether driveline 1126 is connected. For example, in free mode system 1110 can be preprogrammed to operate in a manner to lower the power usage. In various embodiments, connector 1113 is configured as a breakaway connector. Connector 1113 may be configured such that driveline 1126 can be removed only after a force above a selected threshold is applied. Examples of a breakaway connector are described in U.S. Pat. No. 8,794,989 filed Dec. 8, 2011; U.S. Pat. No. 8,894,561 filed Mar. 5, 2013; U.S. Pat. No. 9,387,285 filed Oct. 16, 2015; and U.S. Pat. No. 8,152,035 filed Jul. 6, 2006, the entire contents of which are incorporated herein in their entirety by reference.

With continued reference to FIG. 11, a mechanical circulatory support system 1110 is connected to battery 1122 for powered operation. Batteries 1122 may be external, as shown in FIG. 11, or may be implanted within the subject's body 1112 (e.g., as described above in association with systems 100 and 200). Driveline 1126 exits through the subject's skin via connector 1113 and connects implanted blood pump 1114 to system controller 1120, which monitors system 1110 operation. As noted above, in some embodiments, one or more components of system controller 1120 may be implanted within the subject.

Related controller systems applicable to the systems and methods described herein are described in greater detail in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 1122. It will be appreciated that although system controller 1120 and power source 1122 are illustrated outside/external to the subject body, driveline 1126, system controller 1120 and/or power source 1122 may be partially or fully implantable within the patient, as described above in relation to systems 100 and 200, and as separate components or integrated with the blood pump 1114. Examples of such modifications are further described in U.S. Pat. No. 8,562,508 and U.S. Patent Publication No. 2013/0127253, all of which are incorporated herein by reference for all purposes in their entirety.

The systems described herein (e.g., systems 100 and 200) may be configured to generate an alert upon detecting a disconnection of connector 1113 (e.g., disconnection of external connector 104 from internal connector 106 (shown in FIG. 1), disconnection of power cables 224 and buttons 220 from microconductors 202 and 204 (shown in FIG. 3), etc.). Further, as described above, an internal battery may be used to provide temporary power in the event of a disconnection of connector 1113. In some embodiments, the systems described herein may be configured to operate in a temporary support mode, in which the internal components are able to operate autonomously for a period of time after an intentional or unintentional disconnection of connector 1113.

To facilitate a temporary support mode, in some embodiments, the systems described herein include an internal power source (e.g., a battery) capable of supplying power for a predetermined period of time. In the temporary support mode, the internal power source may be capable of supporting the patient, for example, for at least twenty minutes, at least thirty minutes, at least forty-five minutes, at least one hour, or at least four hours. Accordingly, the patient could disconnect from external power sources for a period of time (e.g., to take a shower, go for a swim, or participate in other activities that might be difficult or impossible for the patient to undertake without disconnection from external power sources). In some embodiments, the internal power source may be capable of supporting the patient for extended periods of time (e.g., approximately four to six hours).

In various embodiments, a cover is provided to cover connector 1113 when driveline 1126 is disconnected. The cover may comprise a sealing assembly to fluidly seal the electrical contacts of connector 1113 to prevent a short, corrosion, and other issues. The sealing assembly may include, for example, one or more hermetic waterproof seals, hermetic waterproof caps, self-healing membranes, and/or other suitable structures capable of preventing exposure from the contacts to the environment. For example, in system 100, the sealing assembly may be formed, for example, on microwire holder 114, electrical contacts 116, and/or microneedles 112 (all shown in FIG. 1). In system 200, the sealing assembly may be formed, for example, on microconductors 202 and 204 and/or housing 212 (all shown in FIG. 3).

The systems and methods described herein provide several clinical and technical advantages over at least some known existing transcutaneous power transfer systems. For example, the embodiments described herein use small-diameter conductors to facilitate reducing inflammatory response and risk of infection in a subject. The distribution across a plurality of relatively thin conductors may provide increased redundancy while reducing the amount of current going through each conductor. This can lead to lowering corrosive activity and infection risk. Decreasing the size of the conductors and increasing the number of connections may increase redundancy and mitigate against the risk of a short by faulty connections (e.g., a broken conductor or fluid ingress in the connector). Further, the small-diameter conductors may be replaced and/or relocated periodically to allow previous power transfer sites to heal. Further, as described herein, internal and external components of the transcutaneous power transfer systems described herein are relatively easy to connect and disconnect from one another. For example, in the embodiment shown in FIGS. 1 and 2, the external connector described herein may be replaced by unplugging the microneedle array from the internal connector. If the connection is left open (subject to appropriate clinical treatment to avoid infection, etc.), the small holes from the microneedles can heal and effectively close the exit site. An example where this might be useful is a VAD patient whose heart has recovered. In various embodiments, a first microneedle array is withdrawn and a second replacement microneedle array is inserted to form a connection to the internal connector. In contrast to conventional systems which form a relatively large defect site, the system described herein only forms very small needle holes, facilitating easy connections and disconnections.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A system for supplying power transcutaneously to an implantable device implanted within a subject, the system comprising:
   a first microconductor configured to extend through the subject's skin;
   a second microconductor configured to extend through the subject's skin, wherein the first microconductor and the second microconductor are configured to receive and conduct power generated by an external power source; and
   a control unit configured to be implanted within the subject, the control unit comprising:
      a housing including a septum attached to a case, wherein the septum is able to be pierced and then reform around an object that did the piercing;
      a first electrical contact fully embedded within the septum, the first electrical contact configured to electrically couple to the first microconductor;
      a second electrical contact fully embedded within the septum, the second electrical contact configured to electrically couple to the second microconductor, wherein the first and second electrical contacts are fully embedded within the septum such that multiple sides of each of the first and second electrical contacts are accessible to the first and second microconductors through the septum;
      control circuitry positioned within the housing and electrically coupled to the first and second electrical contacts, the control circuitry configured to control operation of the implantable device; and
      a driveline connector electrically coupled to the control circuitry, the driveline connector configured to transfer power and control signals to the implantable device through a driveline extending between the driveline connector and the implantable device.

2. The system of claim 1, wherein the control circuitry comprises a Bluetooth transceiver configured to communicate with a remote device.

3. The system of claim 1, wherein the first and second electrical contacts each comprise a titanium wool mesh.

4. The system of claim 1, wherein the first microconductor and the second microconductor are coaxial with one another.

5. The system of claim 1, wherein the control circuitry is configured to:
   detect that at least one of the first and second microconductors has become disconnected from the control unit; and
   generate an alert in response to the detection.

6. The system of claim 5, wherein to generate an alert, the control circuitry is configured to generate an audible alert.

7. The system of claim 5, wherein to generate an alert, the control circuitry is configured to cause the control unit to vibrate.

8. The system of claim 1, wherein the first and second microconductors are configured to conduct alternating current power generated by the external power source.

9. The system of claim 1, wherein the control circuitry comprises a battery configured to store power received from the external power source.

10. The system of claim 1, wherein the system is configured to operate in a temporary support mode when the control unit is disconnected from the external power source.

11. A method of implanting a transcutaneous power transfer system in a subject, the transcutaneous power transfer system operable to supply power transcutaneously to an implantable device in the subject, the method comprising:
    implanting a control unit within the subject, the control unit including a housing having a septum attached to a case, a first electrical contact, a second electrical contact, and control circuitry configured to control operation of the implantable, device, the first electrical contact and the second electrical contact both fully embedded within the septum, wherein the septum is able, to be pierced and then reform around an object that did the piercing, wherein the first and second electrical contacts are fully embedded within the septum such that multiple sides of each of the first and second electrical contacts are accessible through the septum, and wherein the control unit further includes a driveline connector electrically coupled to the control circuitry, the driveline connector configured to transfer power and control signals to the implantable device through a driveline extending between the driveline connector and the implantable device;

inserting a first microconductor through the skin of the subject such that the first microconductor electrically contacts the first electrical contact;

inserting a second microconductor through the skin of the subject such that the second microconductor electrically contacts the second electrical contact; and supplying power to the first and second microconductors from an external power source.

12. The method of claim 11, wherein the first and second microconductors are coaxial with one another, and wherein inserting the first and second microconductors comprises inserting the first and second microconductors simultaneously.

13. The method of claim 11, wherein inserting the first microconductor comprises piercing the septum of the housing and electrically contacting a metallic mesh with the first microconductor.

14. The method of claim 11, wherein inserting the first microconductor comprises inserting the first microconductor using an injection tool that includes a hollow injector barrel housing the first microconductor and a handle coupled to the hollow injector barrel.

* * * * *

UNITED STATES PATENT AND TRADEMARK OFFICE
CERTIFICATE OF CORRECTION

PATENT NO. : 11,197,990 B2
APPLICATION NO. : 15/874026
DATED : December 14, 2021
INVENTOR(S) : Agarwal et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this
Thirty-first Day of January, 2023

Katherine Kelly Vidal
*Director of the United States Patent and Trademark Office*